(12) United States Patent
Grimes

(10) Patent No.: US 6,783,553 B2
(45) Date of Patent: Aug. 31, 2004

(54) PROSTHESIS

(76) Inventor: James B. Grimes, 1921 18th St., Bakersfield, CA (US) 93301

( * ) Notice: Subject to any disclaimer, the term of this patent is extended or adjusted under 35 U.S.C. 154(b) by 149 days.

(21) Appl. No.: 09/999,632

(22) Filed: Oct. 24, 2001

(65) Prior Publication Data

US 2003/0078670 A1 Apr. 24, 2003

(51) Int. Cl.$^7$ .................................................. A61F 2/32
(52) U.S. Cl. .................................................. 623/23.21
(58) Field of Search .......................... 623/16.11, 18.11, 623/22.11, 23.11, 22.15, 23.21–23.31, 23.44, 20.34

(56) References Cited

U.S. PATENT DOCUMENTS

| | | | |
|---|---|---|---|
| 2,622,592 A | | 12/1952 | Rosenstein |
| 2,650,588 A | | 9/1953 | Drew |
| 2,679,245 A | * | 5/1954 | Timmermans ............ 623/23.11 |
| 2,682,265 A | | 6/1954 | Collison |
| 2,685,877 A | | 8/1954 | Dobelle |
| 2,785,673 A | | 3/1957 | Anderson |
| 2,947,308 A | | 8/1960 | Gorman |
| 3,965,490 A | | 6/1976 | Murray et al. |
| 4,530,114 A | | 7/1985 | Tepic |
| 4,546,501 A | | 10/1985 | Gustilo et al. |
| 4,661,112 A | * | 4/1987 | Muller ..................... 623/23.22 |
| 4,664,668 A | | 5/1987 | Beck et al. |
| 4,795,473 A | | 1/1989 | Grimes |
| 4,998,937 A | | 3/1991 | Grimes |
| 5,007,931 A | * | 4/1991 | Smith ......................... 623/23.3 |
| 5,035,717 A | * | 7/1991 | Brooks ..................... 623/23.44 |
| 5,163,964 A | * | 11/1992 | Lazzeri et al. ............ 623/23.21 |
| 5,169,401 A | | 12/1992 | Lester et al. |
| 5,314,479 A | | 5/1994 | Rockwood, Jr. et al. |
| 5,376,125 A | | 12/1994 | Winkler |
| 5,387,244 A | * | 2/1995 | Breard ..................... 623/23.15 |
| 5,458,651 A | | 10/1995 | Lawes |
| 5,480,452 A | | 1/1996 | Hofmann et al. |
| 5,489,310 A | * | 2/1996 | Mikhail ................... 623/19.11 |
| 5,507,829 A | | 4/1996 | Thongpreda et al. |
| 5,571,203 A | | 11/1996 | Masini |
| 5,658,349 A | | 8/1997 | Brooks et al. |
| 5,702,483 A | | 12/1997 | Kwong |
| 5,725,595 A | | 3/1998 | Gustilo |
| 5,755,805 A | | 5/1998 | Whiteside |
| 5,980,575 A | | 11/1999 | Albrektsson et al. |
| 6,273,915 B1 | | 8/2001 | Grimes |
| 6,332,896 B1 | * | 12/2001 | Hubbard et al. ......... 623/23.24 |
| 6,355,069 B1 | * | 3/2002 | DeCarlo et al. .......... 623/23.26 |

FOREIGN PATENT DOCUMENTS

| | | | | |
|---|---|---|---|---|
| DE | 201 04 312 U1 | 5/2001 | | |
| EP | 0 012 146 A1 | 6/1980 | | |
| EP | 0539036 | * | 4/1993 | ............. A61F/2/36 |
| FR | 1 099 519 | 9/1955 | | |
| FR | 1 432 116 A | 3/1966 | | |
| FR | 2 528 307 A | 12/1983 | | |
| FR | 2 638 350 A | 5/1990 | | |
| GB | 2 203 943 | 11/1988 | | |
| WO | WO 97/25939 A1 | 7/1997 | | |
| WO | WO 00/48535 A1 | 8/2000 | | |

* cited by examiner

Primary Examiner—Kevin Shaver
Assistant Examiner—Michael B. Priddy
(74) Attorney, Agent, or Firm—Senniger Powers

(57) ABSTRACT

A prosthesis for implantation in a bone includes a collar having a first surface and a second surface generally on an opposite side of the collar for engaging the bone and transferring forces to the bone. A neck extends outwardly from the first surface and is adapted to receive a ball thereon. A stem extends outwardly from the second surface of the collar for reception in the bone. The second surface is shaped to promote force transmitting engagement of the second surface with the bone over at least a substantial portion of the second surface, to limit engagement of the second surface with the bone at an area of stress concentration in the second surface, and to inhibit line contact between the second surface and bone.

28 Claims, 5 Drawing Sheets

PROSTHESIS

BACKGROUND OF THE INVENTION

The present invention relates to an implantable prosthesis for implantation in a bone such as a femur.

Applicant's prior U.S. Pat. No. 6,273,915 (the '915 patent), which is incorporated herein by reference, is directed to a femoral head-neck prosthesis and method of implantation. The prosthesis comprises a neck mounted on a collar which rests against the femoral neck. A stem is mounted on the underside of the collar to extend generally downward through the femur. In the method of implantation, a seat is formed in the femoral neck to engage the underside of the collar. The shape of the seat is complementary to that of the underside of the collar. If the underside of the collar and the seat are congruent, the entire area of the seat should engage the underside of the collar so that there is 100 percent bone contact at the interface for transmitting substantially 100 percent of the loading. However, greater force may be transmitted to the bone at the intersection of the stem and collar due to line contact between the bone and the stem-collar intersection. According to Wolff's law, changes in stress or force distribution eventually cause alterations in the internal structure of the bone. Those portions of the bone subject to a lesser stress than before are likely to deteriorate and those subject to greater stress than before are likely to thicken. Accordingly, if there is greater stress at the stem-collar intersection, bone there will thicken and will also accumulate so that stress at the intersection steadily increases over time, while stress transmission through the collar at locations spaced from the intersection steadily decreases and bone at such locations deteriorates or "resorbs". The bone may resorb to such an extent that replacement of the implant will be required.

Ideally, a femoral prosthesis should allow for a broad range of motion after implantation. Conventional prostheses may limit the range of hip motion because the neck of the prosthesis impinges or contacts the acetabulum when the femur is pivoted to some positions. Thus, it would be desirable if the neck could be formed to allow a broader range of motion.

In a non-cemented femoral prosthesis, the prosthesis should be fixed in the bone to inhibit movement about axes perpendicular to the longitudinal axis of the prosthesis. As disclosed in the '915 patent, the stem of the prosthesis may include splines to suitably fix the prosthesis. It would be desirable to include additional structure for fixing the prosthesis in the bone, e.g., to further inhibit lateral and medial movement about axes perpendicular to the longitudinal axes.

SUMMARY OF THE INVENTION

Among the several objects and features of the present invention may be noted the provision of a prosthesis which promotes force transmitting engagement of the prosthesis with the bone; the provision of such a prosthesis which inhibits line contact between the prosthesis and bone; the provision of such a prosthesis which inhibits bone resorption; the provision of such a prosthesis which allows a significant range of motion of the joint after implantation; and the provision of such a prosthesis which inhibits prosthesis movement about axes perpendicular to the longitudinal axis after implantation.

Briefly, apparatus of this invention is a prosthesis for implantation in a bone comprising a collar having a first surface and a second surface generally on an opposite side of the collar for engaging the bone and transferring forces to the bone. A neck extends outwardly from the first surface and is adapted to receive a ball thereon. A stem extends outwardly from the second surface of the collar for reception in the bone. The second surface is shaped to promote force transmitting engagement of the second surface with the bone over at least a substantial portion of the second surface, to limit engagement of the second surface with the bone at an area of stress concentration in the second surface, and to inhibit line contact between the second surface and bone.

In another aspect of the invention, a femoral prosthesis comprises a collar having a first surface and a second surface generally on an opposite side of the collar for engaging the femur and transferring forces to the femur. A neck extends outwardly from the first surface and is adapted to receive a ball thereon. A stem extends outwardly from the second surface of the collar for reception in the femur. The second surface includes a recess adjacent to the stem to promote force transmitting engagement of the second surface with the femur over at least a substantial portion of the second surface and to inhibit contact with the femur generally at a location where the stem intersects the collar to thereby inhibit bone resorption.

In yet another aspect of the invention, the femoral prosthesis comprises a neck including a recessed portion to inhibit contact with the acetabulum upon implantation in the femur.

In still another aspect of the invention, the femoral prosthesis comprises a collar including a laterally outwardly facing surface extending generally perpendicular to the first surface and the second surface. The surface has a partial cylindrical shape generally complementary to a resected portion of the lateral neck to thereby inhibit movement about axes perpendicular to the longitudinal axis upon implantation in the femur.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
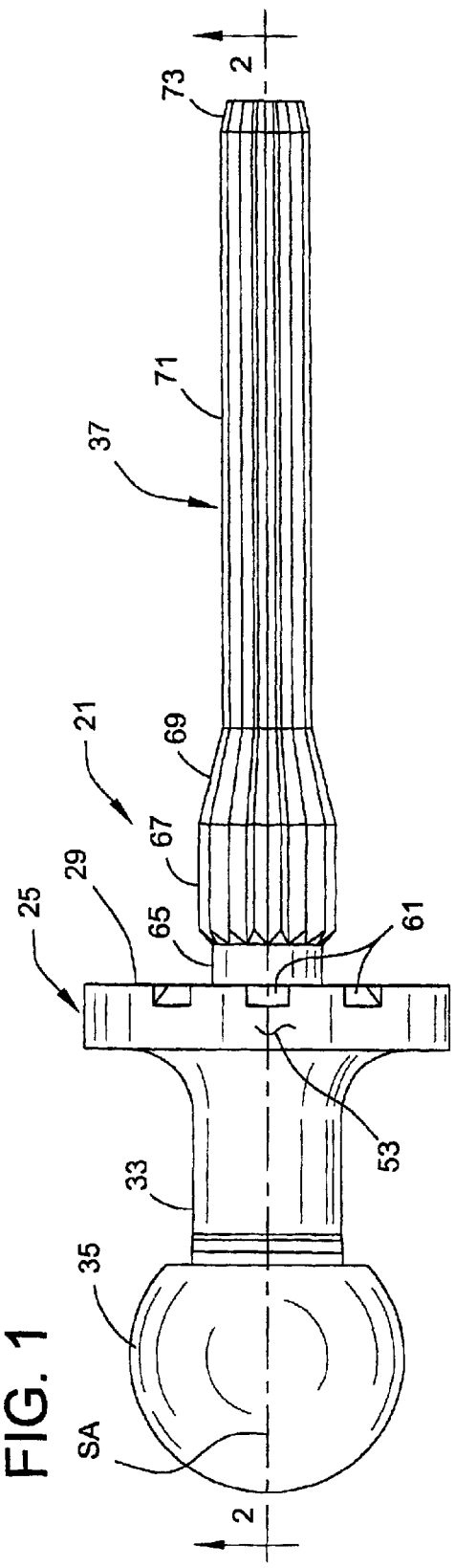
FIG. 1 is a side elevational view of a prosthesis of this invention.

Referring now to the drawings and in particular to FIGS. 1, 1A and 2–3, a transosseous, non-cemented prosthesis of the present invention is designated in its entirety by the reference numeral 21. In this embodiment of the invention, the prosthesis is suitably sized and shaped for implantation in a femur F, though it is to be understood that the prosthesis may be sized and shaped for implantation in other bones, e.g., the humerus. The femur includes a femoral shaft S, a femoral head H, neck N, an intertrochanteric line TL and a greater trochanter T at the upper end of the shaft at the lateral side of the femur. The femur F has a hard layer of cortical bone C adjacent the surface of the bone, relatively soft cancellous bone SC and endosteum (not shown) inside the femur. The prosthesis is made of cobalt-chrome alloy, e.g., warm worked cobalt-chrome alloy in accordance with American Society of Testing and Materials (ASTM) standard 1537, titanium or other suitable material. As implanted, the transosseous prosthesis 21 extends generally from the resected femoral neck N diagonally across the medullary canal MC and out an opposite side of the femur. The prosthesis will usually extend out posterolaterally, but will extend laterally or anterolaterally in cases of neutral version or retroversion, respectively. It should be noted that some features of the prosthesis may be incorporated into non-transosseous, intramedullary prostheses. The prosthesis 21 is of the type which need not be cemented into the femur F, but is secured by mechanical interconnection of the prosthesis with the bone, as described more fully in the '915 patent and hereinafter. Note that it is contemplated to use cement with the prosthesis 21, e.g., at the proximal or upper femoral neck. The prosthesis is constructed so that it is securely held in the bone from rotation (about its longitudinal axis) and toggling (perpendicular to the longitudinal axis, i.e., anterior-posterior and medial-lateral) motion, while permitting axial micromotion to achieve a natural bone loading condition thereby to preserve the bone.

The prosthesis 21 comprises a continuous, circumferential collar generally designated 25 having an upper surface 27 and a lower surface 29 generally on an opposite side of the collar from the upper surface. The lower surface 29 is sized and shaped to engage the bone (e.g., cortical and cancellous bone of the femur F) and transfer forces to the bone. A neck 33 extends outwardly from the upper surface 27 and is adapted to receive a ball 35 thereon. A stem 37 extends outwardly from the lower surface 29 of the collar for reception in the femur (generally, bone) and defines a stem axis SA. In the preferred embodiment, the collar 25, neck 33 and stem 37 are formed as one piece.

Figure 5:
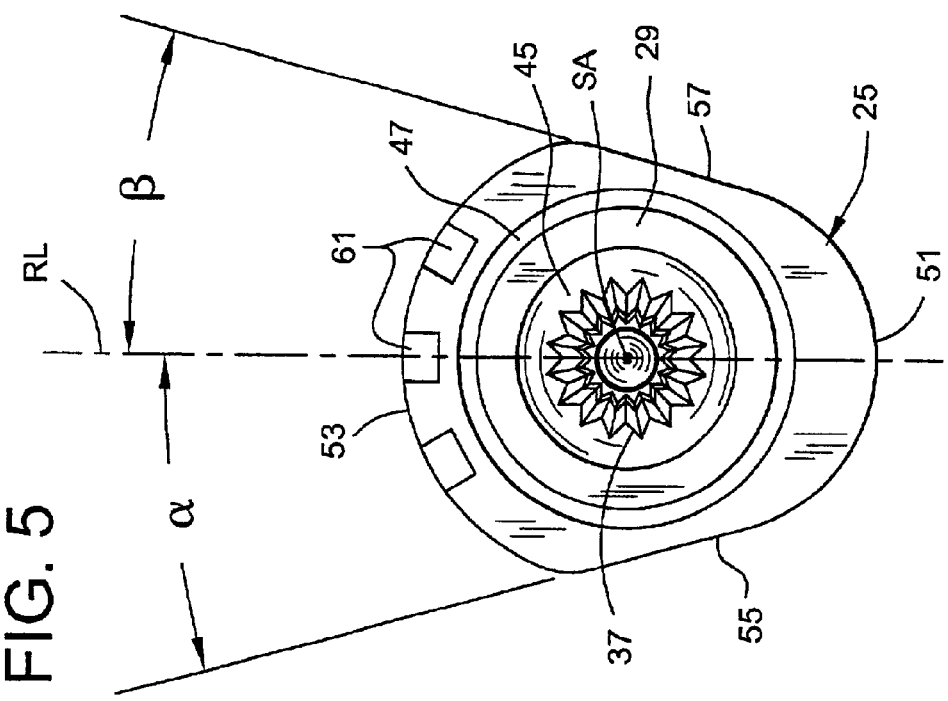
FIG. 5 is an end view of the prosthesis.
Figure 6:
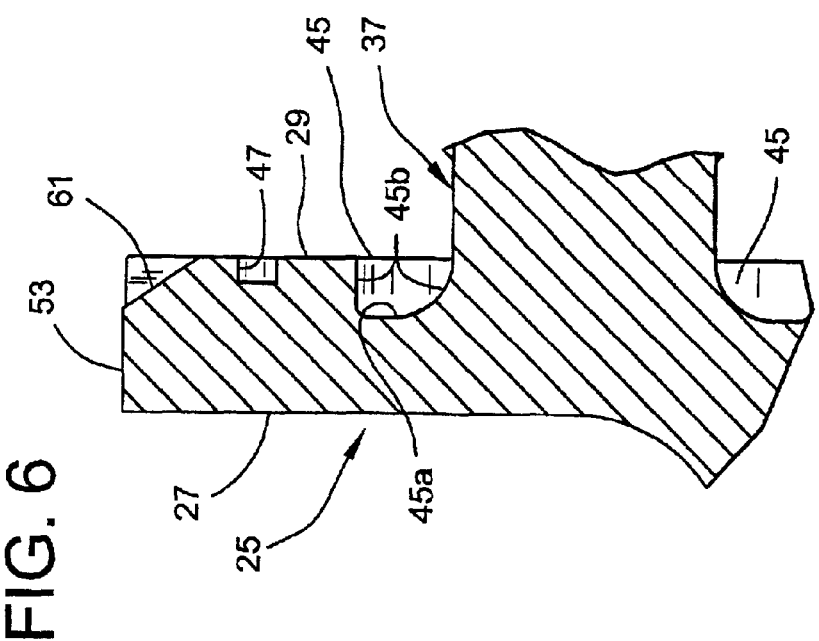
FIG. 6 is an enlarged view of a portion of FIG. 2 corresponding to oval 6 and showing portions of the collar and the stem, the femur being omitted for clarity.

Referring to FIGS. 1, 2, 5 and 6, in this embodiment the lower surface 29 of the collar 25 is generally planar to promote force transmitting engagement of the lower surface with a generally planar resected seat ST formed on the resected femoral neck N over at least a substantial portion of the lower surface. The lower surface 29 is suitably shaped to inhibit line contact between the lower surface and bone and to inhibit contact with the femur F generally at a location where the stem 37 intersects the collar 25. The intersection of the collar 25 and the stem 37 is under relatively high stress after implantation and consequently a stress concentration can occur at the intersection. Thus, there is preferably a radius (also referred to as a fillet) at the intersection so that the stress or force is distributed over a greater area so as to inhibit the effect of the stress concentration and inhibit failure of the prosthesis at the intersection. However, such a radius adds prosthesis material at the intersection which may transmit stress to the bone. Accordingly, the lower surface 29 preferably has an inner recess 45 disposed at the intersection with the stem 37 and extending around the circumference of the stem. The inner recess 45 suitably has an annular channel shape having a web 45a and two flanges 45b with radii at the intersections of the web and flanges (FIG. 6). The inner recess 45 is suitably formed by machining and is preferably positioned at the intersection of the stem and the collar. The inner recess 45 may, however, be spaced somewhat from the intersection. The inner recess 45 of this embodiment is between about 1 mm and about 4 mm deep and is between about 3 mm and about 10 mm wide. The recess 45 is relatively wide and relatively deep to prevent bone from contacting the prosthesis 21 at the stem-collar intersection to thereby inhibit stress transmission through the collar 25 at the stem-collar intersection. Stress is transmitted from the lower surface 29 to the seat ST over a substantial portion of the lower surface-seat interface to promote natural loading of the femur and to inhibit bone resorption. Note that even if bone grows into the inner recess 45 after implantation (which is unlikely), such bone will likely not receive significant stress transmitted through the collar 25.

The lower surface 29 preferably includes an annular outer recess 47 spaced radially outwardly from the inner recess 45. As shown in FIG. 6, the outer recess 47 is preferably shallower and narrower than the inner recess and is suitably about 1 mm deep and about 1.5 mm wide. After implantation, bone preferably grows into the outer recess 47 to further fix the prosthesis from movement. Such bone ingrowth helps to absorb shear forces placed on the prosthesis after implantation. Note that the shape of the recess 47 is not critical and other shapes, such as a U-shaped recess is contemplated. Also, other "macrotexturing" such as recess 47 is contemplated, including, e.g., multiple discrete cylindrical holes and radially arrayed channels. "Microtexturing" such as roughening the lower surface 29 by grit-blasting or coating the surface with a porous material is also contemplated.

Figure 4:
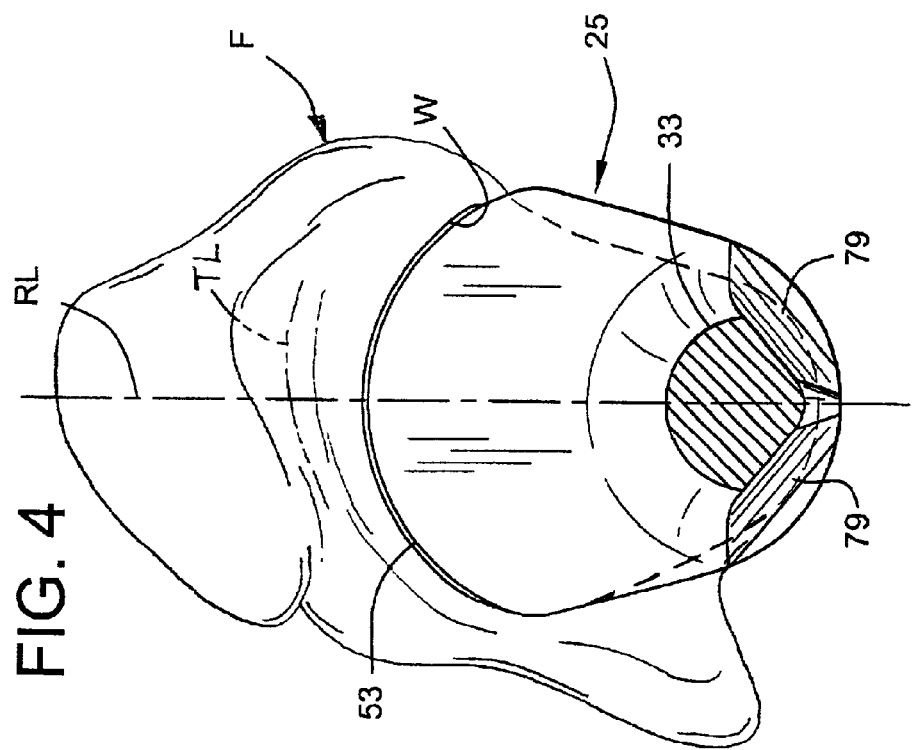
FIG. 4 is a sectional view taken in the plane of line 4—4 of FIG. 3 and showing the prosthesis implanted in the femur.

Referring to FIGS. 4 and 5, the collar 25 extends outwardly laterally, anteriorly, medially and posteriorly. As described in the '915 patent, the collar caps the medullary canal. A medial surface 51 and a lateral surface 53 of the collar each have an arcuate, partial cylindrical shape to completely cover the resected femoral neck N. The axis of the partial cylinder of the lateral surface 53 is co-linear with the stem axis SA, though the axis may also be parallel or otherwise offset so that the shape of the lateral surface may further inhibit rotation upon implantation. In this embodiment, the axis of the partial cylinder of the medial surface 51 is parallel to the stem axis SA (and offset medially). The radius of the partial cylinder of the lateral surface 53 is larger than that of the medial surface to conform generally to the shape of the femur and the resected seat ST. As implanted, the lateral surface 53 preferably engages a concave semi-cylindrical wall W formed in the resected portion of the femur to inhibit toggling motion, especially medial-lateral toggling motion. A reference line RL (FIG. 5) bisects the lateral and medial surfaces and is perpendicular to the stem axis SA. An anterior surface 55 of the collar 25 is generally flat and is angled outwardly at an angle $\alpha$ relative to the vertical reference line RL (FIG. 5). A posterior surface 57 of the collar is generally flat and is angled outwardly at an angle $\beta$ relative to the reference line RL. In this embodiment, the angles $\alpha$ and $\beta$ are both about 15 degrees. Prostheses 21 may be constructed with varying angles to allow fitting one of the prostheses to a patient so that the collar fully covers the resected femoral neck N but does not overhang the neck excessively. For example, it is contemplated that the angles can vary between about 10 and about 20 degrees, and angle $\alpha$ may be significantly greater than angle $\beta$ or vice versa.

Referring to FIGS. 1, 5 and 6, the lateral surface 53 of the collar 25 is formed with at least one angled flat 61 (generally, a recess) which promotes bone ingrowth upon implantation and thereby inhibits rotation of the prosthesis after implantation in the femur. The lateral surface 53 of this embodiment includes three flats 61, each flat angled downward toward the stem 37 at about 45 degrees and suitably formed by machining the lateral surface. During implantation, bone fragments are preferably placed into the flats 61 to encourage bone ingrowth after implantation. It is contemplated that the lateral surface include any number of recesses to promote bone ingrowth. Generally, the lateral surface preferably includes macrotexturing such as the flats 61 and may include further macrotexturing such as grooves, holes, slots or a knurled finish. The lateral surface 53 and the lower surface 29 may also include microtexturing, e.g., the surfaces may be roughened by grit-blasting or coating the surface with a porous material. The lateral surface 53 may also include one or more projections (generally, "positive relief") for penetrating the bone and inhibiting rotation.

Figure 3:
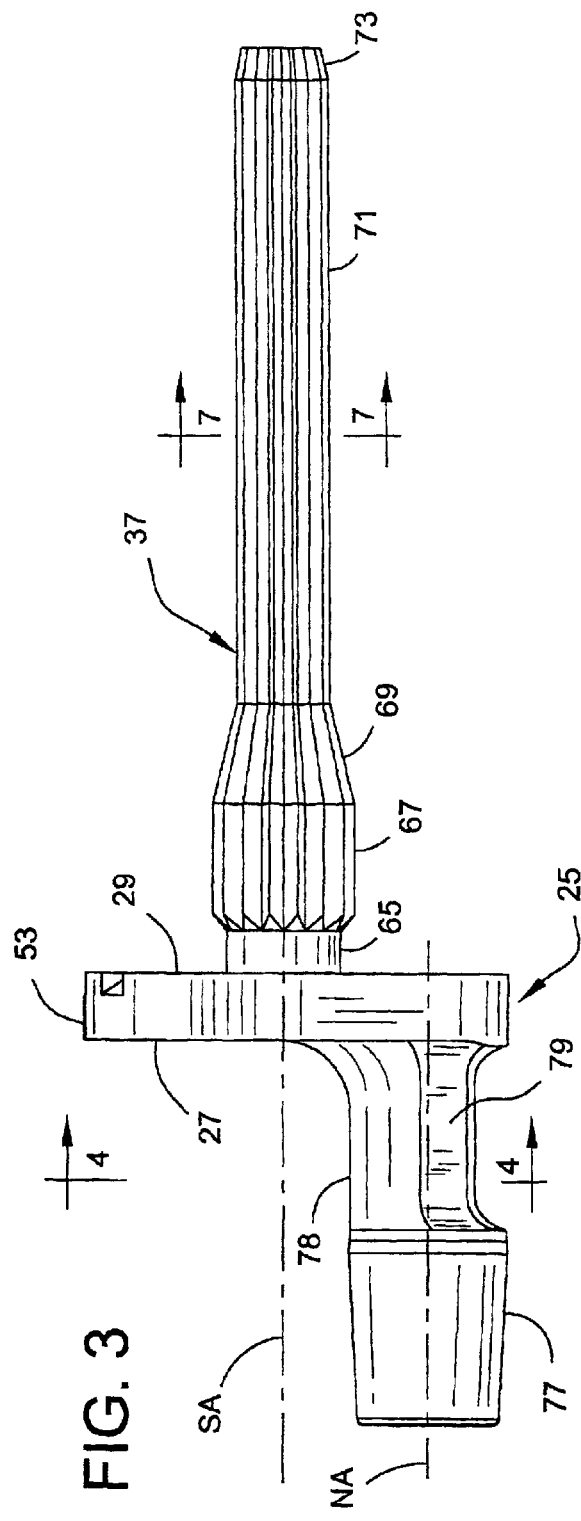
FIG. 3 is a front elevational view of the prosthesis.
Figure 1A:
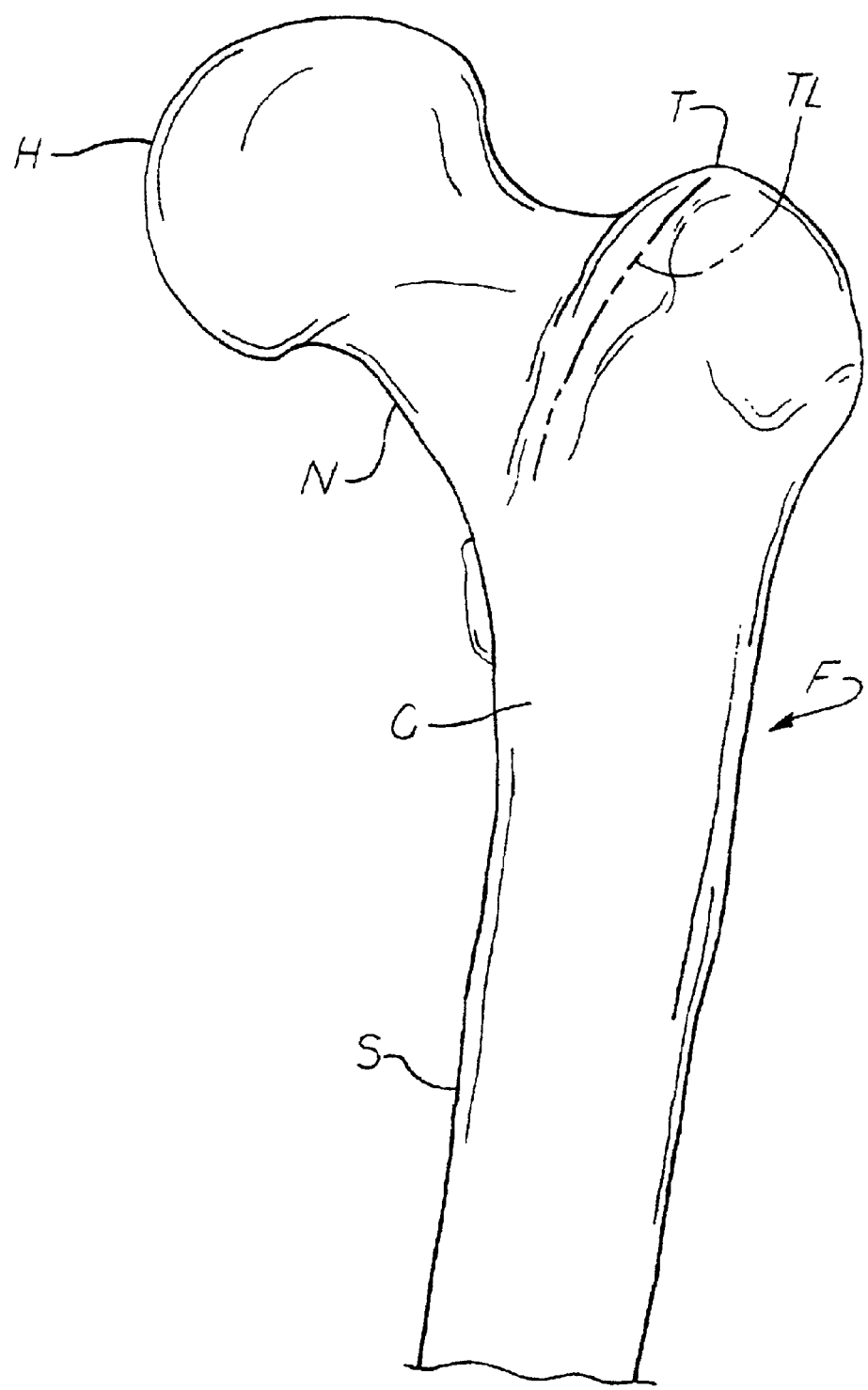
FIG. 1A is an elevational view of an intact femur.
Figure 2:
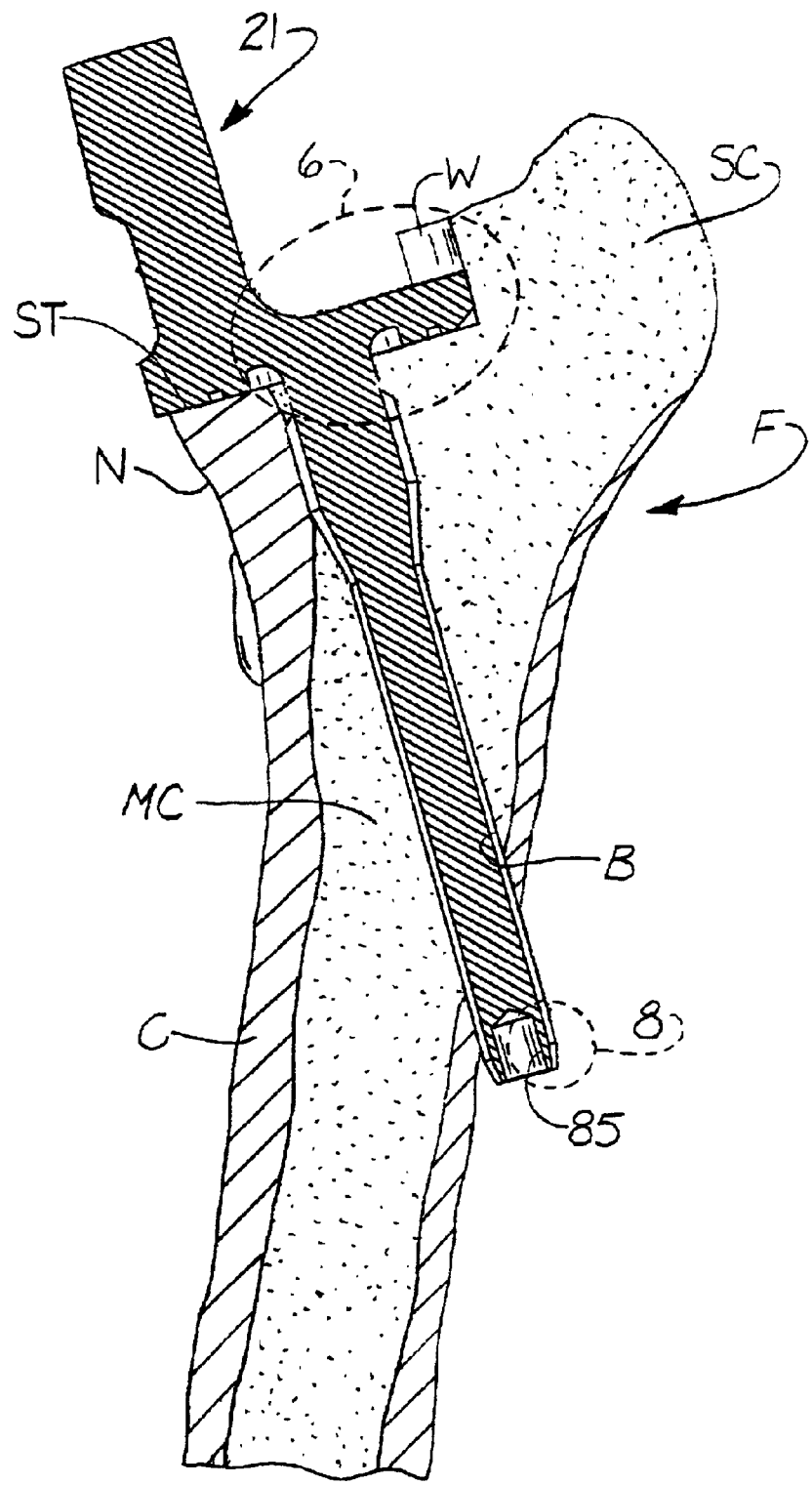
FIG. 2 is a sectional view taken in the plane of line 2—2 of FIG. 1 and showing the prosthesis implanted in a femur.
Figure 7:
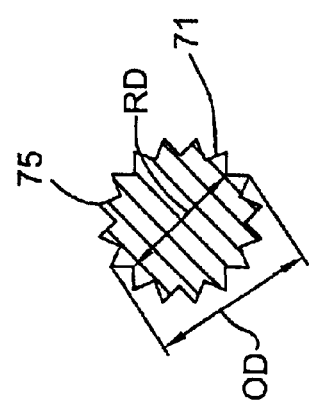
FIG. 7 is a sectional view taken in the plane of line 7—7 of FIG. 3.

Referring to FIGS. 1–3, the stem 37 extends perpendicularly from the lower surface 29 of the collar 25. The portion of the stem 37 closest to the intersection of the stem and collar 25 is suitably a smooth cylindrical portion 65, which may be modified to include a recess (not shown) at or adjacent the intersection with the stem 37. Such a recess can be used in addition to or instead of the inner recess 45 to inhibit line contact between the lower surface and bone and to inhibit contact with the femur generally where the stem intersects the collar. Note that the smooth cylindrical portion having a smaller diameter than that of the adjacent stem is advantageous because a saw guide or the saw template 127 shown in FIGS. 19B–D of the '915 patent may be used with less risk of the saw contacting the stem. Describing the stem 37 from left to right as viewed in FIG. 1, the stem includes the smooth cylindrical portion 65, an upper portion 67, a tapered portion 69 (all of which may generally be described as proximal portions of the stem), a central portion 71 and an end portion 73 (the central and end portions constituting distal portions of the stem). The radially outwardly facing surfaces of the upper portion 67, tapered portion 69 and central portion 71, all of which are disposed for engaging a bore B (described in the '915 patent as bore B1) formed in the interior of the femur F, are, broadly, "fixation surfaces." The upper portion 67, tapered portion 69, and central portion 71 are sized for a close fit within the femur F and each portion has longitudinally extending splines 75 (see FIG. 7) which penetrate the bone inside the femur to secure the prosthesis 21 in the femur F. The end portion 73 is tapered and also has splines 75 (FIG. 8) which can penetrate the bone at the bore B through the posterolateral femoral cortex C to ease insertion of the prosthesis and to inhibit fracture of the bone. As is apparent, the splines 75 extend substantially the entire length of the stem. The splines 75 hold the prosthesis 21 securely against rotational movement about the longitudinal axis SA of the prosthesis after implantation, and encourage bone growth between the splines. However, although the splines 75 resist axial displacement of the prosthesis 21 relative to the femur F, the splines do not rigidly fix the prosthesis against axial micromotion.

Figure 8:
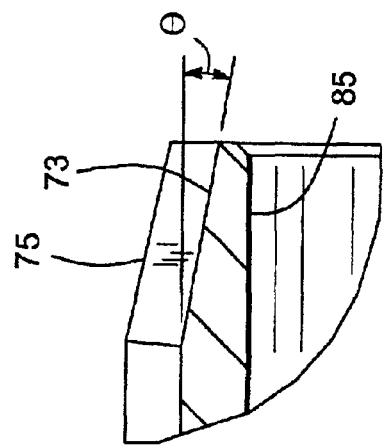
FIG. 8 is a fragmentary enlarged view of a portion of FIG. 2 corresponding to circle 8 and showing the stem end portion.

Referring to FIG. 8, the end portion of the stem 37 is preferably tapered at an acute angle Θ relative to the central portion, the angle preferably being between about five and fifteen degrees. A hole 85 is preferably formed in the end portion to receive a guide tip, such as the bullet-shaped guide tip 125 shown in FIG. 18N of the '915 patent. Optionally, and as shown in the '915 patent, the stem tip may be cut at an angle so that it is generally aligned with or parallel to the outer surface of the femur F on the posterolateral side. The end portion 73 preferably extends outwardly from the posterolateral side of the femur F to inhibit bone growth over the end portion. Such bone growth could undesirably fix the prosthesis 21 in an axial direction and prevent the natural loading at the upper end of the femur by the collar 25.

Referring to FIG. 1, the upper portion 67 preferably has a larger diameter than the central portion 71 to contact the endosteal (inner surface) cortex of the femoral neck N anteriorly, medially and posteriorly and to cause the splines 75 of the upper portion 67 to bite into the cortical bone to inhibit rotation and toggle. Prostheses 21 are constructed with varying upper portion diameters so that one of the prostheses may be selected to fit the patient to achieve optimal cortical contact. The upper portion typically has an outer diameter of between about 11 mm and about 20 mm, and the central portion 71 has an outer diameter OD of about 8.5 mm. The tapered portion 69 is preferably tapered at a relatively shallow angle, e.g., about 10–20 degrees. It is contemplated that the upper portion 67 could include two overlapping cylindrical elements, as shown in the '915 patent.

Referring to FIGS. 3 and 4, the neck 33 has an upper portion 77 having a frustoconical shape and a lower portion 78. The neck has a longitudinal axis NA parallel to the longitudinal axis SA of the stem, as described in the '915 patent. The lower portion 78 is generally cylindrical but includes two flat recessed portions 79 which inhibit contact of the neck with the acetabulum upon implantation in the femur F to prevent impingement or interference of the neck with the acetabulum upon flexing of the joint, as well as hip adduction and hip extension. When the prosthesis 21 is implanted, one of the recessed portions 79 is positioned posteromedially and the other recessed portion is positioned anteromedially. In this embodiment, the flat recessed portions extend generally parallel to the axis NA and are symmetrically sized and positioned about reference line RL. Preferably, the recessed portions 79 reduce the posteromedial and anteromedial portions of the neck 33 so that the range of motion of the hip joint is improved compared to conventional hip prostheses. An additional 10 to 20 degrees of flexion (average of about 15 degrees) is to be expected over conventional hip prostheses, the exact improvement depending in part on the angle at which the prosthesis 21 is implanted, the size of the prosthesis and the size and shape of a prosthetic cup (not shown) in the acetabulum. Flexion is defined as motion of the hip causing the knee to move generally vertically toward the chest.

The prosthesis 21 is suitably implanted in a manner similar to one of the implantation methods shown and described in the '915 patent. Note that such methods are suitably modified for implantation of the prosthesis 21. Generally, the angle of the medial trabecular stream TS (FIGS. 4A and 18A of the '915 patent) is determined and used to position the prosthesis 21. The stem 37 of the prosthesis 21 is to be aligned with the average compression loading vector for the particular femur F to assure close replication of normal loading of the femur (i.e., loading prior to implantation of the prosthesis). The angle guide (similar to angle guide 29 in the '915 patent) is positioned as described with respect to FIG. 18B of the '915 patent, anteversion is determined, and then a saw guide (not shown), similar to saw guide 41, is secured in the angle guide sleeve 33 to make a horizontal cut to resect the femoral head H. The saw guide is preferably not extended as far from the angle guide as is shown in FIGS. 4B and 18C of the '915 patent so that more of the base of the head H is resected. Also, the saw does not cut as much bone laterally as is shown in FIGS. 4B and 18C so that more of the femoral lateral neck N is preserved, as shown in FIG. 2 of the present application. A vertical cut is made free hand or by use of the saw guide so that sufficient bone remains for the lateral surface 53 to engage the neck.

The proximal neck is free-hand reamed using successive reamers, each having a larger diameter than the previous reamer, to achieve cortical bone contact (FIGS. 18D and 18E of the '915 patent). A pointer on the angle guide serves as a directional indicator during reaming. The bore B formed by the reamer is not as large in diameter as that shown in the '915 patent because the prosthesis 21 does not include overlapping cylinders as shown in the '915 patent. Sizing of the bore B for the best fitting prosthesis 21 is performed as described with respect to FIG. 18F, except that a proximal sizer (not shown) is used, similar to sizer 113, which does not include the overlapping cylinder in the upper portion. The proximal sizer typically has a diameter between 8 and 25 mm. A guide pin similar to guide pin 119 is introduced to drill through the cortex, similar to the method shown in FIGS. 4N and 18F of the '915 patent, except that the tube 49 is not used, and instead the proximal sizer remains in the bore B for receiving a pin guide similar to pin guide 117. The proximal sizer has a bore therein which receives the pin guide and the guide pin, and the cortex is drilled. The method is further performed as described with respect to FIGS. 8J–K to drill the cortical tunnel, preferably using an 8.0 mm cortical drill.

The planer (not shown) for implanting the prosthesis 21 preferably has a flat bottom corresponding to the planer 81' shown in the '915 patent so as to form a generally planar seat ST. The planer is also suitably shaped to form the concave partial cylindrical wall W in the lateral portion of the neck adjacent the greater trochanter (FIG. 2), i.e., the planer is cylindrical-shaped. The planer is employed similar to the method described with respect to FIG. 18M, except that the trunnion and guide described therein are replaced with a suitably sized one-piece guide that extends through the cortical tunnel. As shown in FIG. 2 of the present application, the planer forms the seat ST in the neck N so that the partial cylindrical wall W is adjacent the greater trochanter T, but does not substantially contact or substantially crossover the intertrochenteric line TL (FIG. 1A) so that the greater trochanter T is left intact. It is contemplated however that a portion of the greater trochanter be resected as described in the '915 patent and that the lateral surface of the prosthesis 21 be extended further laterally to engage the greater trochanter.

Prior to implantation, the guide tip described above is installed in the hole 85 in the stem 37. The bullet-nosed shape of the guide tip helps to keep the prosthesis from hanging up on the bone before it passes through the posterolateral femoral cortex. As discussed in the '915 patent, the prosthesis (without the ball 35) is then implanted by driving the stem into the bore B as shown in FIG. 2. The bore B through the posterolateral cortex is smaller than the outer diameter of the central portion 71 of the stem 37 so that the splines 75 bite into the bone. Preferably, the bore B is about 0.5 mm smaller than the outer diameter of the stem. The bore B through the femoral neck N is preferably about 1.0 mm smaller than the upper portion 67 of the stem so that the splines 75 bite into the bone, especially the cortical bone. Note that a root diameter RD of the splines on the upper portion 67 (not shown) and the central portion (FIG. 7) is less than the bore B diameter. The stem end portion 73 protrudes through the oblique hole in the posterolateral cortex so that cortical bone does not later grow over the end of the stem 37. The lower surface 29 of the collar 25 is substantially congruent with the seat ST as described above, and the lateral surface 53 substantially engages, or is at least adjacent to, the femoral wall W. If necessary, congruency between the seat ST and the lower surface 29 may be improved by use of the saw template 127 shown and described with respect to FIGS. 19B–D of the '915 patent.

Once the prosthesis 21 is implanted, an appropriately sized ball 35 is then locked onto the neck. The ball 35 is received in the acetabulum or a prosthetic cup in the acetabulum.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A femoral prosthesis for implantation in a femur, the prosthesis comprising:
   a collar having a first surface and a second surface generally on an opposite side of the collar,
   a stem extending outwardly from the second surface of the collar for reception in the femur, the stem being configured for transosseous implantation in which the stem enters the femur generally at one side thereof, crosses a medullary canal and enters cortical bone on an opposite side of the femur, and
   a neck extending outwardly from the first surface and adapted to receive a ball thereon, the neck including a recessed portion to inhibit contact with an acetabulum upon implantation in the femur.

2. A femoral prosthesis as set forth in claim 1 wherein the neck has a longitudinal axis generally parallel to a longitudinal axis of the stem.

3. A prosthesis for implantation in a bone, the prosthesis comprising:
   a collar having a first surface and a second surface generally on an opposite side of the collar for engaging the bone and transferring forces to the bone,
   a neck extending outwardly from the first surface and adapted to receive a ball thereon, and
   a stem extending outwardly from the second surface of the collar for reception in the bone,
   the second surface of the collar being shaped to promote force transmitting engagement of the second surface with the bone over at least a substantial portion of the second surface, to limit engagement of the second surface with the bone at an area of stress concentration in the second surface, and to inhibit line contact between the second surface and the bone.

4. A prosthesis as set forth in claim 3 wherein the second surface is shaped to inhibit contact with the bone generally at a location where the stem intersects the collar.

5. A prosthesis as set forth in claim 4 wherein the second surface has a recess adjacent to the stem.

6. A prosthesis as set forth in claim 5 wherein the recess is annular and extends around a periphery of the stem.

7. A prosthesis as set forth in claim 3 wherein a laterally outwardly facing surface of the collar is formed to promote bone ingrowth and thereby inhibit rotation of the prosthesis upon implantation in the bone.

8. A prosthesis as set forth in claim 7 wherein the laterally outwardly facing surface includes at least one flat.

9. A prosthesis as set forth in claim 8 wherein the laterally outwardly facing surface of the collar has a partial cylindrical shape for mating with a resected portion of a femoral lateral neck.

10. A prosthesis as set forth in claim 3 wherein the prosthesis is adapted for implantation in a femur and wherein the neck is sized and shaped to inhibit contact with the acetabulum upon implantation in the femur.

11. A prosthesis as set forth in claim 10 wherein the neck includes a recessed portion to inhibit contact with the acetabulum upon implantation in the femur.

12. A prosthesis as set forth in claim 3 wherein the prosthesis is adapted for implantation in a femur, and wherein the stem has axially extending splines formed thereon for fixing the prosthesis from movement about its longitudinal axis and about axes perpendicular to the longitudinal axis and to inhibit axial fixation of the stem upon implantation in a femur.

13. A prosthesis as set forth in claim 12 wherein the splines extend substantially the length of the stem.

14. A prosthesis as set forth in claim 13 wherein the stem is generally cylindrical, a proximal portion of the stem having a larger diameter than a distal portion of the stem.

15. A femoral prosthesis for implantation in a femur, the prosthesis comprising:
a collar having a first surface and a second surface generally on an opposite side of the collar for engaging the femur and transferring forces to the femur,
a neck extending outwardly from the first surface and adapted to receive a ball thereon, and
a stem extending outwardly from the second surface of the collar for reception in the femur,
the second surface of the collar including a recess adjacent to the stem to promote force transmitting engagement of the second surface with the femur over at least a substantial portion of the second surface and to inhibit contact with the femur generally at a location where the stem intersects the collar to thereby inhibit bone resorption.

16. A femoral prosthesis as set forth in claim 15 wherein the recess is annular and extends around a periphery of the stem.

17. A femoral prosthesis as set forth in claim 15 wherein a laterally outwardly facing surface of the collar includes at least one indentation to promote bone ingrowth and thereby inhibit rotation of the prosthesis upon implantation in the femur.

18. A femoral prosthesis as set forth in claim 17 wherein the laterally outwardly facing surface of the collar has a partial cylindrical shape for mating with a resected portion of a lateral neck of the femur.

19. A femoral prosthesis as set forth in claim 15 wherein the neck includes a recessed portion to inhibit contact with an acetabulum upon implantation in the femur.

20. A femoral prosthesis for implantation in a femur having a femoral neck and a resected portion, the prosthesis comprising:
a collar having a first surface, a second surface generally on an opposite side of the collar for engaging the femoral neck and a laterally outwardly facing surface extending generally perpendicular to the first surface and the second surface,
a neck extending outwardly from the first surface and adapted to receive a ball thereon, and
a stem extending outwardly from the second surface of the collar for reception in the femur, the stem defining a longitudinal axis of the prosthesis,
the laterally outwardly facing surface being adapted to at least partially engage the resected portion upon implantation in the femur, being formed to promote bone ingrowth and having a partial cylindrical shape generally complementary to the resected portion to thereby inhibit movement about axes perpendicular to the longitudinal axis upon implantation in the femur.

21. A femoral prosthesis as set forth in claim 20 wherein the laterally outwardly facing surface includes recesses to promote bone ingrowth and thereby inhibit rotation.

22. A femoral prosthesis as set forth in claim 20 wherein the stem has axially extending splines formed thereon to further fix the prosthesis from movement about axes perpendicular to the longitudinal axis and for fixing the prosthesis from movement about its longitudinal axis.

23. A prosthesis for implantation in a bone, the prosthesis comprising:
a collar having a first surface and a second surface generally on an opposite side of the collar for engaging the bone and transferring forces to the bone,
a neck extending outwardly from the first surface and adapted to receive a ball thereon, and
a stem extending outwardly from the second surface of the collar for reception in the bone,
the second surface of the collar being shaped to inhibit contact with the bone generally at a location where the stem intersects the collar.

24. A prosthesis as set forth in claim 23 wherein the second surface has a recess adjacent to the stem.

25. A prosthesis as set forth in claim 24 wherein the recess is annular and extends around a periphery of the stem.

26. A prosthesis as set forth in claim 23 wherein the stem is configured for transosseous implantation in which the stem enters the femur generally at one side thereof, crosses a medullary canal and enters cortical bone on an opposite side of the femur.

27. A prosthesis for implantation in a bone, the prosthesis comprising:
a collar having a first surface and a second surface generally on an opposite side of the collar for engaging the bone and transferring forces to the bone,
a neck extending outwardly from the first surface and adapted to receive a ball thereon, and
a stem extending outwardly from the second surface of the collar for reception in the bone, the stem being configured for transosseous implantation in which the stem enters the femur generally at one side thereof, crosses a medullary canal and enters cortical bone on an opposite side of the femur,
the second surface of the collar being shaped to promote force transmitting engagement of the second surface with the bone over at least a substantial portion of the second surface, to limit engagement of the second surface with the bone at an area of stress concentration in the second surface, and to inhibit line contact between the second surface and the bone.

28. A prosthesis as set forth in claim 27 wherein the second surface has a recess for inhibiting line contact between the second surface and the bone.

* * * * *